(12) United States Patent
McMorrow

(10) Patent No.: US 6,773,406 B2
(45) Date of Patent: Aug. 10, 2004

(54) NON-INVASIVE SURROGATE BLADDER PRESSURE INDICATION SYSTEM

(75) Inventor: Gerald J. McMorrow, Duvall, WA (US)

(73) Assignee: Diagnostic Ultrasound Corporation, Redmond, WA (US)

( * ) Notice: Subject to any disclaimer, the term of this patent is extended or adjusted under 35 U.S.C. 154(b) by 665 days.

(21) Appl. No.: 09/737,066

(22) Filed: Dec. 13, 2000

(65) Prior Publication Data

US 2003/0171692 A1 Sep. 11, 2003

(51) Int. Cl.$^7$ ............................ A61B 5/00; A61B 5/103; A61B 8/00
(52) U.S. Cl. .................... 600/561; 600/587; 600/438
(58) Field of Search .......................... 600/29, 300, 437, 600/438, 446, 449, 561, 587; 73/861

(56) References Cited

U.S. PATENT DOCUMENTS 4,852,578 A * 8/1989 Companion et al. ........ 600/449
4,926,871 A * 5/1990 Ganguly et al. ............ 600/443
5,235,985 A * 8/1993 McMorrow et al. ........ 600/443
5,592,941 A * 1/1997 McMorrow ................. 600/443
5,964,710 A * 10/1999 Ganguly et al. ............ 600/449

* cited by examiner

Primary Examiner—Charles Marmor
(74) Attorney, Agent, or Firm—Jensen & Puntigam, P.S.

(57) ABSTRACT

The system includes a bladder volume device which determines the volume of urine in the bladder on a non-invasive basis, such as by ultrasound. The device then compares the volume determination, which is made on a regular basis, against previously obtained cystometry information for the patient, which comprises a graph which correlates bladder pressure, specifically detrusor pressure, against volume of urine in the bladder. The graph is used by the system to produce a surrogate bladder pressure for each volume determination made. The system then provides an indication of the surrogate bladder pressure so that the patient can determine when catheterization is desirable.

12 Claims, 2 Drawing Sheets

US 6,773,406 B2

NON-INVASIVE SURROGATE BLADDER PRESSURE INDICATION SYSTEM

TECHNICAL FIELD

This invention relates generally to bladder pressure measurement and/or monitoring systems, and more specifically concerns a system for determining a surrogate bladder pressure value using previously determined cystometry information.

BACKGROUND OF THE INVENTION

The physical condition of high bladder pressure, eventually leading to over-distention of the bladder and typically caused by overfilling of the bladder, can in some cases lead to severe physical consequences, including bladder muscle damage, kidney cell damage and elevated blood pressure. With respect to bladder muscle damage, small tears can result in the bladder muscle and bladder wall, producing some tissue death in the bladder wall. In the kidneys, overfilling of the bladder can lead to back pressure which is transmitted through the ureters back into the kidneys, compromising the capillary profusion in the glomerulus (urine producing) portion of the kidneys, which often results in permanent damage to the kidneys. High bladder pressure can also have severe physiological effects within the bladder, including high infection rate, possible diverticula formation and stone formation.

Overfilling of the bladder can have a number of causes, including lack of attention to a patient who is under anesthesia during lengthy surgery. Overfilling is common in patients who experience some degree of bladder dysfunction, caused by injury (e.g. spinal cord injury), various bladder diseases, or other more general disorders which affect the bladder, including muscular sclerosis (MS), Parkinson's disease and other diseases. Further, certain surgical procedures, such as prostate surgery, can result in the interruption (severing) of nerves to the bladder, which leads to bladder dysfunction. Still other causes include normal aging, as well as certain anxiety disorders.

All of the above factors can in some way affect or disrupt the coordination between the sphincter muscles and the bladder which account for the timely emptying of the bladder. The above bladder conditions, particularly for those situations, such as a severe spinal cord injury, where there is no sensation of bladder fullness at all, are treated by a technique referred to as intermittent catheterization. This can be done on a time basis, at precise time intervals; in many cases, however, the time basis approach results in more frequent catheterizations than necessary, which increases the chances of infection in the bladder area. In other cases, catheterization is not performed frequently enough, such as for smaller bladders. This leads to distention of the bladder.

Intermittent catheterization can also be performed using volume information determined by an external non-invasive device which measures the volume of urine in the bladder. However, the volumetric approach may, in some cases, not be optimum relative to the actual pressure in the bladder. Bladder pressure most likely provides the most accurate and the most appropriate basis for making a decision to perform a catheterization at a specific point in time. Up to this point, however, bladder pressure information has been available only through a quite invasive medical procedure, which cannot in practice be done on a sufficiently regular basis to be used for routine catheterization decisions.

SUMMARY OF THE INVENTION

Accordingly, the present invention includes a system and corresponding method for providing an indication of bladder pressure for a patient comprising: a bladder volume determining system for obtaining, i.e. determining, the volume of urine in the bladder of a patient; means comparing the bladder volume determination against a previously determined cystometry graph of bladder pressure versus bladder volume for the patient, so as to determine surrogate bladder pressure values from said bladder volume determinations; and an indicator for indicating said surrogate pressure.

BEST MODE FOR CARRYING OUT THE INVENTION

The system of the present invention is used to determine what is referred to herein as a "surrogate" bladder pressure value at regular intervals during the day. The bladder pressure information is used to make appropriate decisions concerning catheterization of the bladder at specific times. The system thereby provides protection against bladder distention, while at the same time reducing the risk of infection caused by the catheterization procedure by providing more accurate information to the user concerning when a bladder catheterization is actually necessary, and thereby typically reducing the number of catheterizations during a given time period.

The present system first requires the development of a cystometry graph/chart for each patient. The development of a cystometric graph is a well known procedure, which is described in some detail in the following text, the contents of which are hereby incorporated by reference: SMITH'S GENERAL UROLOGY, 13th Ed, Appleton & Lang 1992, Ch. 27, *Neuropathic Bladder Disorders*.

Basically, in a cystometry procedure, a first catheter, which includes a filling lumen portion and a pressure sensor portion, is directed into the bladder of the patient, through the urethra. The bladder is then completely emptied through the catheter. A second catheter with a pressure sensor is inserted through the anus of the patient into the abdominal region. A saline solution is then pumped into the bladder through the first catheter, while pressure in the bladder is measured by the pressure sensor on the first catheter. The pressure within the abdomen (abdominal pressure) is measured by the pressure sensor on the second catheter. Both pressure measurements are taken at selected volume (saline solution) increments.

At the same time, the patient's bladder sensation bladder is noted, if the patient has any feeling relative to bladder function. For a normal person, this is typically divided into a weak sensation, a strong sensation and a very strong urge (sensation) to urinate. For a person with a severe bladder condition, there will be little or no sensation. A graph is then made with one axis (the Y axis) being bladder muscle pressure, sometimes referred to as detrusor pressure, which is the internal bladder pressure (the pressure measured by the sensor on the first catheter) minus the abdominal pressure. This difference pressure is believed to be the key bladder pressure value, as it represents the pressure on the actual bladder (detrusor) muscle. This value is directly correlatable to bladder distention. On the other axis is the volume of liquid (urine) in the bladder, as determined by measuring the value of the instilled saline solution, usually by means of a weight sensor.

Figure 3:
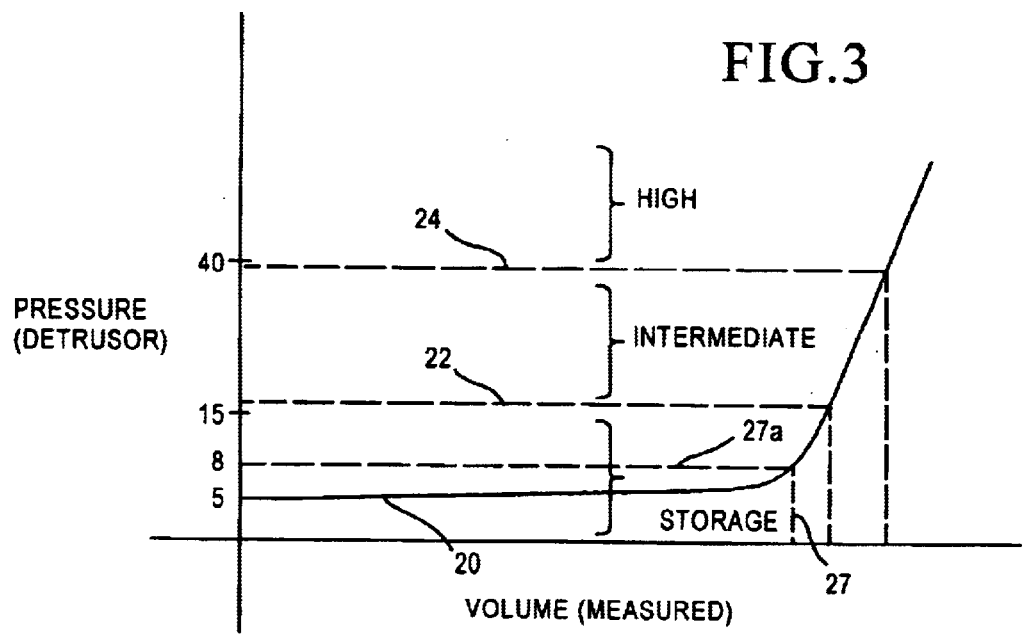
FIG. 3 is a cystometry curve.

An example of such a graph is shown in FIG. 3. Again, the graph compares the volume of urine in the bladder against detrusor pressure. Levels of detrusor pressure are also correlated with appropriate bladder function in FIG. 3. During the "storage" phase of bladder function, the bladder is at a relatively low pressure (shown at line 20 in FIG. 3), allowing urine to be stored in the bladder at a pressure value which is less than the venous pressure in the bladder wall. Under such conditions, the bladder walls have proper blood circulation. A level of pressure above the bladder storage pressure value is specified as an "intermediate" pressure value. A possible intermediate value, shown at line 22, which typically would still be considered normal and not be considered particularly dangerous, is in the pressure range of 5–25 cm. of water. Catheterization would be considered in the higher portion of the intermediate range. Normal pressure should not rise above 40 cm of water, which would be considered in the high range (line 24 in FIG. 3), and indicate a potentially dangerous pressure condition.

Once the cystometry graph has been made, then any pressure level which is in the "high" range would indicate that it is definitely time for a catheterization. It should be understood, however, that these pressure range values could vary somewhat. Current research, however, shows evidence of damage at 40 centimeters of water (cm/$H_2O$).

Once the cystometry graph has been developed for a particular patient, the system of the present invention can then be used to make surrogate pressure determinations for a particular patient using a urine volume determining instrument, as described below.

Figure 1:
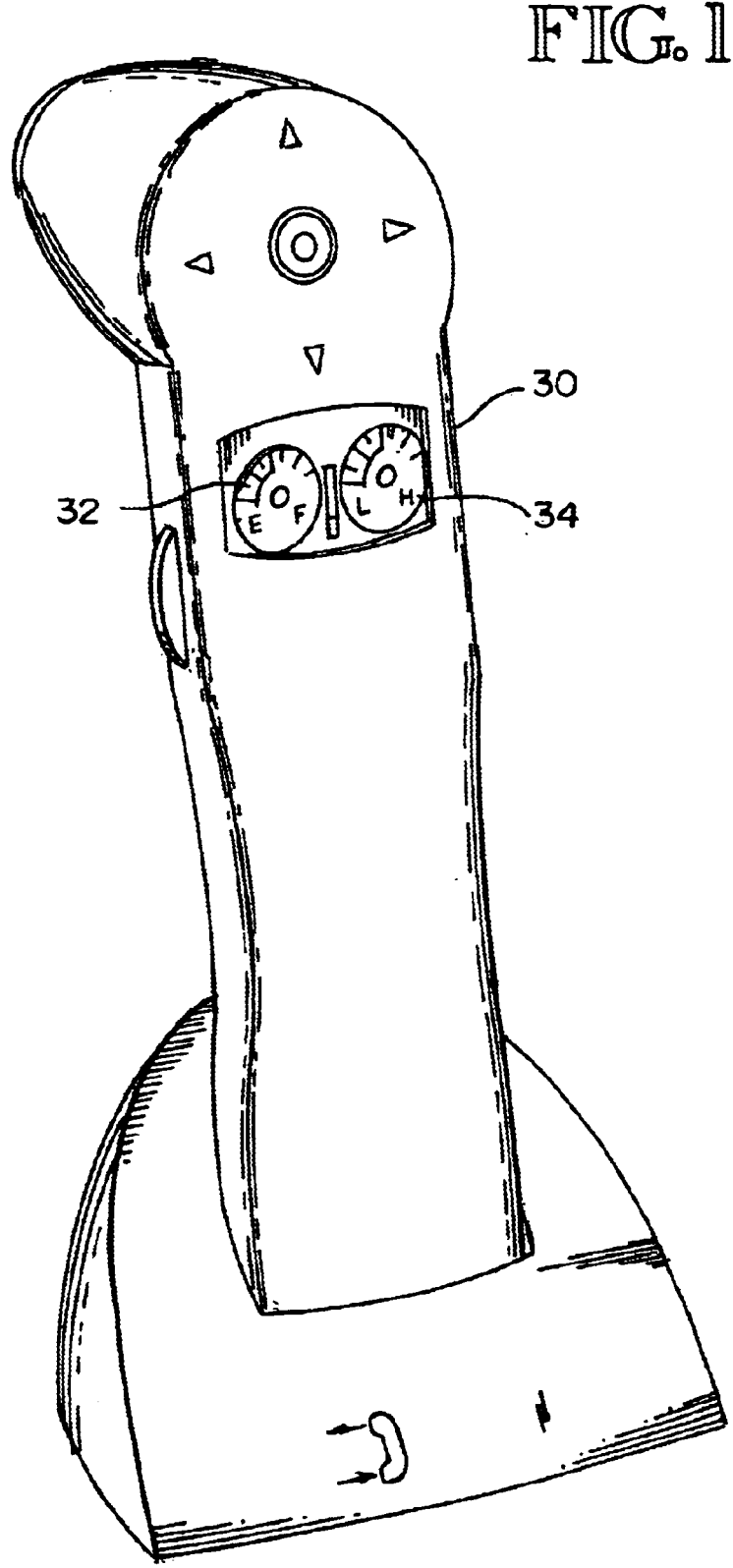
FIG. 1 is a schematic diagram showing the basic instrument of the present invention.

Such a volume determining instrument is shown representationally in FIG. 1. It includes in one case an ultrasound portion for generating, transmitting and receiving ultrasound information concerning the bladder. Such a device useful in both obtaining raw ultrasound information and then using that information to determine the volume of urine in the bladder is described in U.S. Pat. Nos. 4,926,871 and 5,235,985, owned by the assignee of the present invention, the contents of which are hereby incorporated by reference.

In one embodiment of the present invention, such as shown in FIG. 1, the volume of the urine in the bladder is calculated within the device 30 itself, from the raw ultrasound data developed by the device and the volume determining software with the device. The volume information is then shown at one display part 32 of the device. The display can take a number of forms, preferably easy to read and understand by the user. In FIG. 1, the display involves a half-circle bar which varies between empty (E) and full (F) for volume information.

In the embodiment of FIG. 1, cystometry graph information for a particular patient is stored in the device itself. The cystometry information, as indicated above, would have been determined at a particular prior point in time, such as at the time of discharge of the patient from a spinal injury rehabilitation unit, in the case of a spinal injury, as one example. In other cases of bladder dysfunction, such as disease or due to aging, the cystometry information would also have been obtained at a selected previous point in time. The device 30 of FIG. 1 includes a processor which compares the particular volume value determined by the device against the stored cystometry graph information (e.g. FIG. 3) to produce a corresponding bladder pressure value. Referring to the graph of FIG. 3, for example, a measured volume value shown at 27 would result in a pressure value (27a) of approximately 8 cm of water. Again, the patient's particular graph provides a pressure value after a volume value has been determined.

The pressure value so obtained is referred to as a surrogate pressure herein, since the value is not obtained directly, but rather through a determination process using the cystometry graph information stored in the device. The surrogate pressure value is shown in a second display portion 34 of the device 30. In the embodiment shown, this also comprises a half-circle bar, indicating the amount of the pressure, between a low value (L) and a high value (H). The display can be graded between those values so that the patient can readily determine where he/she is with respect to pressure, including the safe regions of storage and intermediate pressure levels and the more dangerous high pressure level.

The FIG. 1 displays are, of course, examples of one kind of display; actual numerical values can be used as well. Furthermore, different indications can be provided to the user, such as bar graphs or color indications of volume and pressure values. Selected indicators can be used which indicate a "high" pressure, dangerous condition or a condition approaching that level. This can be done through visual or audio means.

When the pressure display is in the intermediate region, moving toward the high region, the patient then knows that it is an appropriate time to plan for catheterization. If the pressure is high, there is the strong possibility of bladder damage and immediate catheterization is called for. In the case of each patient, a particular appropriate pressure level can be selected for catheterization which is not dangerous but is high enough to avoid the risks of too-frequent catheterizations. When it is time for catheterization, the patient or a caregiver inserts a catheter into the urethra of the patient (male or female) and voiding of the bladder occurs. In accordance with standard procedure, care is taken to minimize the possibility of infection during the catheterization process. As indicated above, the appropriate frequency of catheterizations are more accurately determined using bladder pressure as the determining standard.

Figure 2:
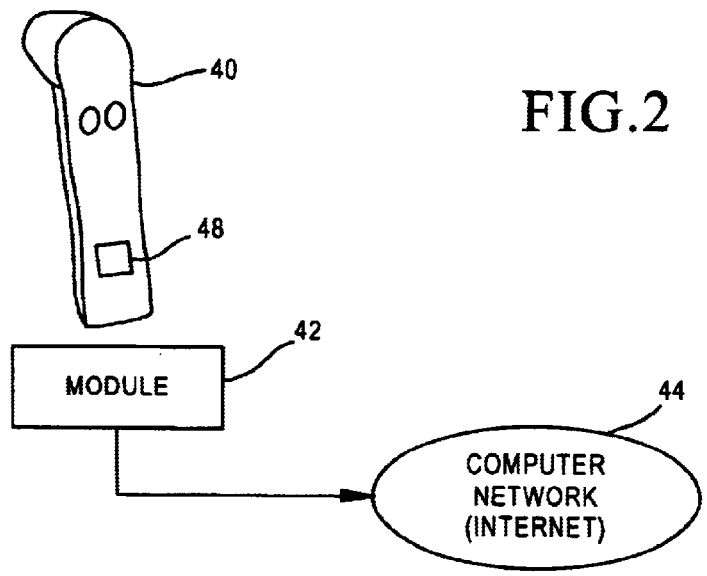
FIG. 2 is a diagram showing one embodiment of the present invention which involves a connection to the internet.

FIG. 2 shows the arrangement for two other embodiments of the present invention. Both of these embodiments utilize a device shown generally at 40 for obtaining raw ultrasound data concerning the volume of urine in the bladder, similar to that described above for device 30 of FIG. 1. The system of FIG. 2, however, includes an internet capability, involving an internet module 42 which includes a modem and browser for connection to the internet 44 and in particular an internet site associated with the system.

In one variation of the embodiment of FIG. 2, device 40 includes a processing capability to calculate the volume of urine in the bladder from the ultrasound raw data, like a conventional bladder volume instrument. In this embodiment, the calculated volume of urine is then transmitted through the internet connection to a website server which includes the cystometry graph information for the particular patient with the transmitted volume information. The calculation of surrogate pressure is then made at the website and transmitted back through the internet connection to the device 40, which displays the transmitted pressure information in the manner described above.

In a variation of this embodiment, device 40 only has the capability of obtaining the raw ultrasound data. This data is then transmitted to the website, where the volume of urine in the bladder is first calculated and then the surrogate pressure determined, using the cystometry graph for the patient with the volume information. Both the bladder volume and the bladder pressure information are then transmitted back to device 40 through the internet connection, where they are displayed.

In all three embodiments (FIGS. 1 and 2), however, the information concerning pressure which is available at a display device is utilized by the patient to make decisions as to an appropriate time for catheterization.

It should be understood that the first embodiment could also have an internet connection capability, so that additional/updated information relevant to the patient could be exchanged between the patient and the website. For instance, periodic information concerning the patient could be transmitted to the website, where it can be accumulated in a history report concerning each patient. Each catheterization event can be indicated by the patient by operating a button 48 or the like on, for example, the device 40. This report could then be available to the patient's physician through the physician's own web browser, with access to the website. Such a report can provide statistical data for episodes of high pressure. This can also be used for patient/caregiver instructions relative to correcting the situation.

Further, new, updated cystometry graph information obtained following the initial cystometric graph could be provided by the physician directly to the website for a particular patient, which in turn could provide the updated cystometry information to the patient device, to replace the existing cystometry information.

Hence, the present invention can either be a standalone device or can make use of an internet capability for updating cystometry information, or for various aspects of the actual system itself, such as volume determinations and/or surrogate pressure determinations.

Further, with an internet capability for the device, a service provider could provide a service of pressure determinations on a time basis, i.e. for a monthly charge. The volume determining device itself could then be provided economically to a patient free of charge.

Accordingly, the present invention is a system which determines surrogate pressure in the bladder, which in turn can be used as an accurate indicator of appropriate times for bladder catheterization. The present system of bladder pressure determination is non-invasive, using cystometry graph information. Hence, catheterization decisions can be made accurately, typically reducing the number of catheterizations and thereby reducing the risk of infection, while avoiding the dangers of pressure reaching high levels.

Although a preferred embodiment of the invention has been disclosed herein for purposes of illustration, it should be understood that various changes, modifications and substitutions can be made without departing from the spirit of the invention, which is defined by the claims which follow.

What is claimed is:

1. A system for providing an indication of bladder pressure for a patient, comprising:

a bladder volume determining system for obtaining a bladder volume determination indicative of the volume of urine in the bladder of a patient;

means for comparing the bladder volume determination against a previously determined cystometry graph of bladder pressure versus bladder volume for the patient, so as to determine a surrogate bladder pressure value from said bladder volume determination; and an indicator for indicating said surrogate pressure.

2. A system of claim 1, wherein the cystometry graph is specific for said patient.

3. A system of claim 1, including an internet module for connecting the system to the internet.

4. A system of claim 3, wherein the comparing means is located remotely from the volume determining system at a system website.

5. A system of claim 4, wherein the bladder volume determining system includes a patient-operated device for obtaining ultrasound information about the patient's bladder from which a bladder volume value can be determined and wherein a bladder volume determination is made at the website from the ultrasound information.

6. A system of claim 3, wherein the bladder volume determining system includes a signal element, operable by the patient, for indicating that the patient intends to proceed with a catheterization, and wherein said indication is provided through an internet connection to a system website.

7. A system of claim 3, wherein updated cystometry information is provided to the system through the internet connection.

8. A system of claim 1, wherein said comparing means and said volume determining system are present in a single patient-operated device.

9. A system of claim 1, including an alarm indicator when the surrogate pressure goes above a predetermined level.

10. A system of claim 1, wherein the system provides information concerning the urine volume in the bladder as well as the pressure within the bladder.

11. A method for providing an indication of bladder pressure for a patient, comprising the steps of:

providing a device to a patient which is capable of obtaining ultrasound data concerning the patient's bladder from which the volume of urine in the bladder may be determined;

operating said device to obtain ultrasound data concerning the bladder of the patient;

determining the volume of urine in the patient's bladder from the ultrasound data;

comparing the determined bladder volume of urine against a previously determined cystometry graph of bladder pressure versus bladder volume for the patient, so as to determine a surrogate bladder pressure value from said determined bladder volume of urine in said bladder; and providing an indication of said surrogate pressure to said patient.

12. A method of claim 11, wherein the step of comparing is accomplished by a service provider and the step of providing an indication of surrogate pressure is initiated by the service provider upon completion of the comparing step.

* * * * *

UNITED STATES PATENT AND TRADEMARK OFFICE
CERTIFICATE OF CORRECTION

PATENT NO.    : 6,773,406 B2
DATED         : August 10, 2004
INVENTOR(S)   : Gerald J. McMorrow It is certified that error appears in the above-identified patent and that said Letters Patent is hereby corrected as shown below:

Column 6,
Line 33, -- for indicating -- should be inserted after the word "indicator".

Signed and Sealed this

Twentieth Day of September, 2005

JON W. DUDAS
*Director of the United States Patent and Trademark Office*